(12) United States Patent
Ingber

(10) Patent No.: US 10,152,702 B2
(45) Date of Patent: Dec. 11, 2018

(54) APPARATUS AND METHODS FOR ANALYZING A MEDICAL CONDITION

(71) Applicant: Michael Ingber, Mendham, NJ (US)

(72) Inventor: Michael Ingber, Mendham, NJ (US)

(73) Assignee: Michael Ingber, Mendham, NJ (US)

( * ) Notice: Subject to any disclaimer, the term of this patent is extended or adjusted under 35 U.S.C. 154(b) by 953 days.

(21) Appl. No.: 14/371,155

(22) PCT Filed: Feb. 6, 2013

(86) PCT No.: PCT/US2013/024895
§ 371 (c)(1),
(2) Date: Jul. 8, 2014

(87) PCT Pub. No.: WO2013/119632
PCT Pub. Date: Aug. 15, 2013

(65) Prior Publication Data
US 2014/0349326 A1 Nov. 27, 2014

Related U.S. Application Data

(60) Provisional application No. 61/596,028, filed on Feb. 7, 2012.

(51) Int. Cl.
*G06Q 20/14* (2012.01)
*G06F 19/00* (2018.01)
*G16H 10/40* (2018.01)

(52) U.S. Cl.
CPC ....... *G06Q 20/145* (2013.01); *G06F 19/3418* (2013.01); *G06F 19/3456* (2013.01);
(Continued)

(58) Field of Classification Search
CPC .................................................. G06Q 20/145
See application file for complete search history.

(56) References Cited

U.S. PATENT DOCUMENTS

| 6,330,491 B1 | 12/2001 | Lion |
| 8,655,009 B2 | 2/2014 | Chen et al. |

(Continued)

FOREIGN PATENT DOCUMENTS

| EP | 0699046 B1 | 8/2003 | |
| WO | WO-9424929 A1 * | 11/1994 | ........... A61B 5/0444 |

(Continued)

OTHER PUBLICATIONS

ISA/US International Search Report dated Apr. 24, 2013, for International Application No. PCT/US2013/024895, filed Feb. 6, 2013.

*Primary Examiner* — Robert A Sorey
*Assistant Examiner* — Kristine K Rapillo
(74) *Attorney, Agent, or Firm* — Jones Day

(57) ABSTRACT

Apparatus and methods are provided for analyzing a medical condition of a user. The apparatus may include a user interface configured to receive user identification information inputted by the user, an analyzer, and a processor all disposed within a common housing. The analyzer is configured to receive a biological specimen from the user and to analyze the biological specimen to generate analysis information. The processor is configured to store and forward the analysis information and to receive prescription information. The apparatus may include a communication unit configured to transmit the user identification information and the analysis information to a doctor at a remote location for review and to receive the prescription information from the doctor. The apparatus then may dispense the prescribed medication or print a medication prescription.

18 Claims, 6 Drawing Sheets

(52) U.S. Cl.
CPC ......... *G06F 19/3462* (2013.01); *G16H 10/40* (2018.01); *Y02A 90/26* (2018.01); *Y10T 436/144444* (2015.01); *Y10T 436/146666* (2015.01); *Y10T 436/147777* (2015.01); *Y10T 436/173076* (2015.01); *Y10T 436/200833* (2015.01)

(56) References Cited

U.S. PATENT DOCUMENTS

| | | | | |
|---|---|---|---|---|
| 2003/0190671 A1* | 10/2003 | Leyland-Jones | ....... | B82Y 30/00 435/7.1 |
| 2008/0186499 A1 | 8/2008 | Krauth | | |
| 2009/0125324 A1 | 5/2009 | Keravich et al. | | |
| 2011/0015504 A1* | 1/2011 | Yoo | ...................... | A61B 5/0002 600/301 |

FOREIGN PATENT DOCUMENTS

| | | | | | |
|---|---|---|---|---|---|
| WO | 2004061743 | A2 | 7/2004 | | |
| WO | WO-2004061743 | A2 * | 7/2004 | ........... | G06F 19/321 |
| WO | 2011056888 | A2 | 5/2011 | | |
| WO | WO-2011056888 | A2 * | 5/2011 | ............ | A61M 39/02 |

\* cited by examiner

APPARATUS AND METHODS FOR ANALYZING A MEDICAL CONDITION

I. CROSS-REFERENCE TO RELATED APPLICATIONS

This application claims the benefit of U.S. Provisional Patent Application No. 61/596,028, filed Feb. 7, 2012 and entitled "Apparatus and Methods for Analyzing a Medical Condition," the entire contents of which are incorporated by reference herein.

II. FIELD OF THE INVENTION

This application generally relates to apparatus and methods for analyzing a medical condition by testing a specimen at a local station, transmitting the test results to a remote station for evaluation and diagnosis, and dispensing of medication at the local station.

III. BACKGROUND OF THE INVENTION

Pathogenic bacteria are bacteria that cause bacterial infections. There exists a wide variety of pathogenic bacteria species that contribute to a variety of diseases and infections including bronchitis, diarrhea, diphtheria, ear infections, food poisoning, gonorrhea, leprosy, Lyme disease, meningitis, pink eye, pneumonia, sinus infections, strep throat, syphilis, tetanus, tuberculosis, typhoid fever, ulcers, urinary tract infections, whooping cough, and yeast infections.

Immediate initiation of a therapy, such as administration of antibiotics, is often highly beneficial for treating a bacterial infection. There are circumstances where a person having a bacterial infection is unable or unwilling to visit a doctor in-person for diagnosis. Still, such a person would greatly benefit from, or may even require, treatment.

Some types of bacterial infections are considered 'uncomplicated' and often a person having such an infection recognizes symptoms based on past experiences without visiting a doctor. For example, a person having a urinary tract infection (UTI) may recognize a burning sensation during urination and conclude that they likely have a UTI. The person still must go through the inconvenience of scheduling a doctor's appointment and visiting the doctor for appropriate treatment.

Additionally, a person having a sexually transmitted disease caused by a bacterial infection, such as gonorrhea or syphilis, may feel too embarrassed to visit a doctor in person. A need therefore exists for an apparatus for analyzing a biological specimen, for communicating with a doctor, and for receiving treatment in a location convenient to a user.

Currently, a person having a medical condition seeking treatment generally submits a biological specimen to a doctor in-person for testing and analysis. For example, a doctor may use a machine having a reflectance spectroscope or "reflectometer" to analyze specimens of body fluid to determine the presence of a particular substance in a person's urine such as the machine described in U.S. Patent Pub. No. 2008/0186499 to Krauth, the entire contents of which are incorporated by reference herein. Reflectance spectroscopy uses the linear relationship between absorbance and concentration of an absorbing species (Beer's law), to determine the contents of a specimen. An unknown concentration of an analyte may be determined by measuring the amount of light that a specimen absorbs and applying Beer's law. If the absorptivity coefficient of the analyte is not known, the unknown concentration may be determined using a working curve of absorbance versus concentration derived from standards.

Reflectance instruments may be used to measure important properties and relative levels of key analytes in urine by measuring relative reflectance, usually from various specific pads, on a urine dipstick. Examples of important properties include pH, the presence of blood, and specific gravity. Examples of key urine analytes include, but are not limited to, glucose, urobilinogen, nitrite, and protein. The measured properties and/or analytes may be reviewed by a doctor who then may provide a diagnosis and prescribe an appropriate course of treatment with medication.

With advancements in telemedicine, it is becoming more common to provide clinical health care over a distance using telecommunication and information technologies. U.S. Pat. No. 6,330,491 to Lion describes a system for vending prescription medications using a network of remotely distributed, automated dispensing units. The system includes a remote vending machine (RVM) unit having a plurality of drugs stored therein and coupled to a host computer via a network. A user may input a patient identification key code at the RVM unit that is communicated to the host computer and the RVM unit may dispense prescribed medication to the user.

U.S. Patent Pub. No. 2009/0125324 to Keravich describes a medical product dispensing system including a vending machine having a user interface including a data entry and communication device, an identification device, a biometric data collection device, and a payment device. The biometric data collection device is configured to measure biometric characteristics using an external device that is electrically coupled to the vending machine or by receiving data at the vending machine from an external test or laboratory site. The vending machine also may store and dispense medical products. These previously-known systems suffer from a variety of drawbacks including the lack of communication with a doctor from the vending machine and the inconvenience of having to visit a doctor or laboratory before receiving medication.

There is a need to provide analysis of medical conditions at a location convenient to a user using an apparatus that may communicate with a doctor located at a distance from the apparatus for diagnosis based on the analysis.

IV. SUMMARY OF THE INVENTION

The present invention overcomes the drawbacks of previously-known systems by providing apparatus and methods for analyzing a medical condition of a user as part of a single commercial transaction. The apparatus may be configured to exchange information via a network. The apparatus may include a user interface configured to receive user identification information input by the user, an analyzer, and a processor all disposed within a common housing. The user interface may include, for example, a display, keypad, or touch screen for entering identifying information such as name, age, or drug allergies, as well as payment information or magnetic card reader that permits a user to swipe a credit card. The analyzer may be configured to receive a biological specimen from the user and to analyze the biological specimen to generate analysis information. The processor may be configured to store and forward the analysis information and to receive prescription information.

The communication unit is operatively coupled to the processor and may be configured to transmit the user identification information and the analysis information to a doctor at a remote location for review over a network and to receive prescription information from the doctor over the network. The apparatus then may dispense the prescribed medication using an automated dispensing assembly and/or print a medication prescription using a printer.

The analyzer may analyze the biological specimen, e.g., a urine sample, on a reagent strip and may generate information on leukocytes, glucose, bilirubin, ketone, specific gravity, nitrite, pH, protein, urobilinogen, blood, albumin, creatinine, leukocyte esterase, red blood cells, white blood cells, bacteria, or any combination thereof in the biological specimen. The analysis information may be used by the doctor located at a remote location to diagnose a medical condition such as bronchitis, diarrhea, diphtheria, ear infections, food poisoning, gonorrhea, leprosy, Lyme disease, meningitis, pink eye, pneumonia, sinus infections, strep throat, syphilis, tetanus, tuberculosis, typhoid fever, an ulcer, a urinary tract infection, whooping cough, a yeast infection, acute nonbacterial disease, chronic nonbacterial disease, or any combination thereof.

The apparatus may also include a video camera and display configured to permit the user to conduct a face-to-face consultation with a doctor at a remote location, for example, for an additional fee.

The apparatus may be sized and shaped in a large vending machine-like configuration for placement in public areas or may be sized and shaped in a handheld configuration for personal and/or home use.

In accordance with one aspect of the present invention, a system for analyzing medical conditions is provided comprising a remote doctor workstation, a payment processing center, and an apparatus. The apparatus may be configured to receive user identification information input by the user, to receive payment information, and to generate analysis information from analysis of a biological specimen of the user. The apparatus may include a processor configured to transmit the identification information and the analysis information over a network to the remote doctor workstation and to transmit the user identification information and the payment information to the payment processing center over the network.

The present invention further provides methods for analyzing a medical condition of a user. The method may include receiving a biological specimen from the user at an apparatus; analyzing the biological specimen from the user at the apparatus to generate analysis information; transmitting the analysis information over a network from the apparatus to a doctor for diagnosis; generating prescription information based on the diagnosis; and transmitting the prescription information over the network to the apparatus or to a pharmacy. The apparatus then may dispense a prescribed medication to the user.

Transmitting the analysis information over the network may include transmitting the analysis information to computer readable storage, inputting the computer readable storage into a computer, and transferring the analysis information over the network from the computer to the doctor.

Transmitting the prescription information over the network may include transmitting the prescription information to a computer over the network, transferring the prescription information to computer readable storage, and inputting the computer readable storage into the apparatus.

V. BRIEF DESCRIPTION OF THE DRAWINGS

FIG. 4 shows a perspective, exploded view of an exemplary tray assembly for insertion in the analysis apparatus of FIG. 2, wherein an insert is positioned to hold a reagent cassette.

VI. DETAILED DESCRIPTION OF THE INVENTION

Figure 1:
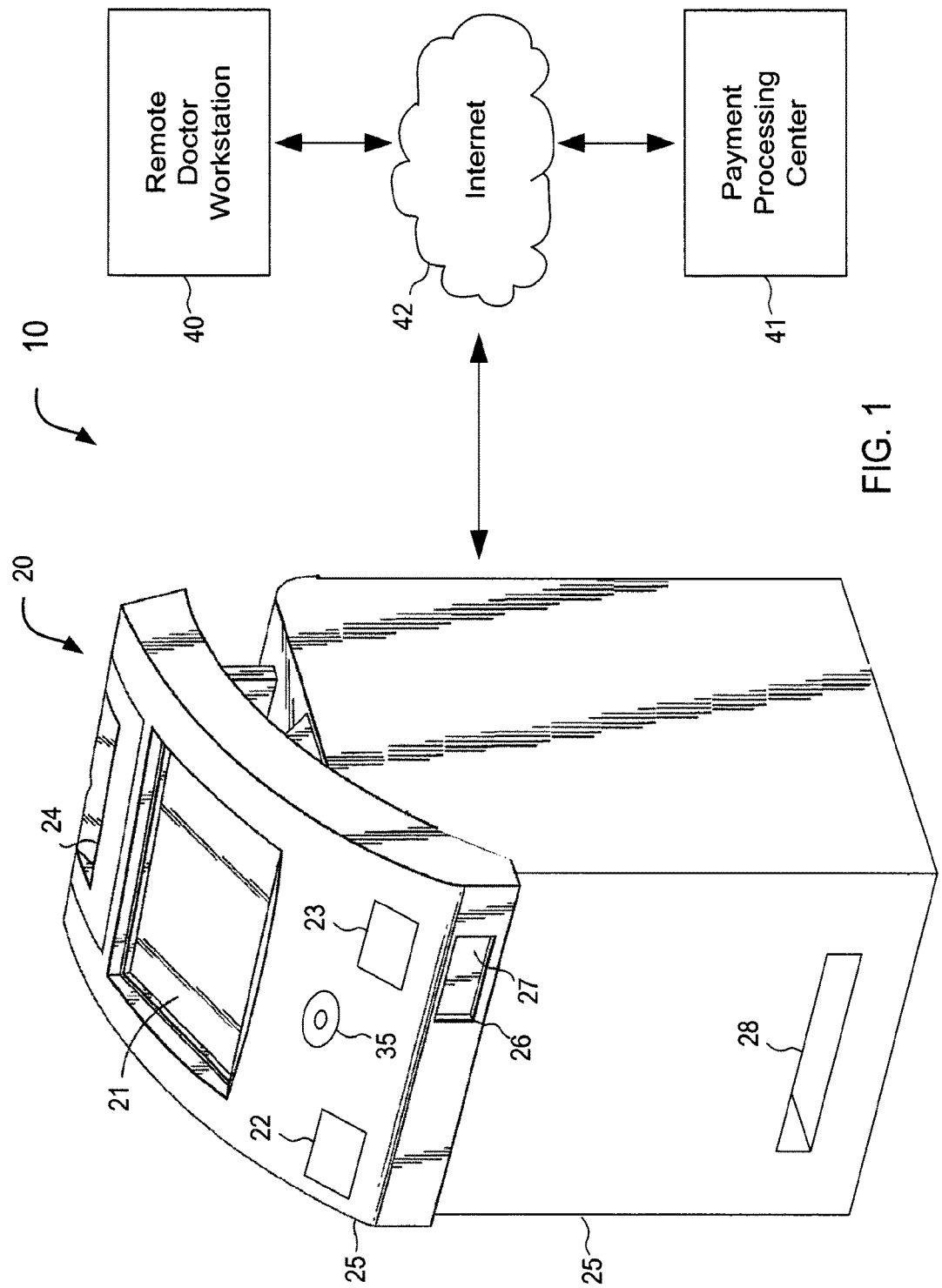
FIG. 1 shows an overview of an exemplary diagnostic system in accordance with the principles of the present invention.

Referring to FIG. 1, an overview of diagnostic system 10 of the present invention is provided, including analysis apparatus 20 operatively coupled to remote doctor workstation 40 and payment processing center 41 via Internet 42 or other suitable network. Analysis apparatus 20 is configured to accept a biological specimen such as a urine sample, to analyze the biological specimen, to transmit the analysis information to remote doctor workstation 40 for review, and to receive prescription information input by a doctor at remote doctor workstation 40 based on the doctor's diagnosis of the analysis information. Advantageously, the components of analysis apparatus 20 may be integrated in a common housing that is placed or readily fitted, in the manner of a kiosk, to available wall space or central floor space at many commercial establishments or other convenient public locations, providing a "one-stop shopping" experience. Apparatus 20 may be positioned in proximity to areas of high pedestrian traffic at a commercial establishment where prescription-needing patients have convenient access or may be positioned in an area having general privacy such a restroom. By way of example only, apparatus 20 might be placed in an available location/restroom in or adjacent to a hospital, doctor's office, pharmacy, or grocery store.

As described in detail below, analysis apparatus 20 is configured to accept a biological specimen from a user and to analyze the biological specimen to generate analysis information. Apparatus 20 then transmits the analysis information over a network, such as Internet 42, or a telephone network to remote doctor workstation 40 for review and payment information input by the user to payment processing center 41. Payment processing center 41 may be an automated system, e.g., that receives credit card information input be the user and debits the user's credit card for the cost of the biological specimen analysis, doctor review, and any medication dispensed by apparatus 20. Alternatively or in addition, payment processing center 41 also may initiate submission of claim forms to the user's medical healthcare insurer, if such information is input by the user. Remote doctor workstation 40 may be a workstation, e.g., a computer(s), cellular phone(s), etc., manned by a doctor selected by the user or a doctor or doctor network associated with apparatus 20. Preferably, at least one doctor in the designated doctor network is available to review analysis information to provide a diagnosis 24 hours a day, 7 days a week.

In one embodiment, remote doctor workstation 40 may be located at a centralized control facility that includes multiple such workstations for monitoring and controlling multiple apparatuses 20 at different locations. Alternatively, remote doctor workstation 40 may be located at a hospital emergency room location, which typically are staffed around the clock.

Remote doctor workstation 40 and payment processing center 41 may receive user identification information from analysis apparatus 20 in an email, text message, at a website, a facsimile, or the like via Internet 42, telephone network, or the like. In addition, for privacy reasons, only remote doctor workstation 40 receives the analysis information generated by analyzing the biological specimen and, where appropriate, the user's relevant medical history information and any information about drug allergies. The appropriate doctor then may review this information, which also may include symptoms inputted by the user, to make a diagnosis. For example, the doctor may review the amount of nitrites, leukocytes, leukocyte esterase, red blood cells, white blood cells, and/or bacteria in a urine sample together with the user's input of "burning during urination" and diagnose that the user has a urinary tract infection. The doctor then may enter diagnosis information and prescription information via remote doctor workstation 40. Diagnosis information may include the name of the diagnosed disease/infection and optionally a description on the same. Prescription information may include, for example, sufficient information for a pharmacy to fill a prescription or may include sufficient information to inform a user that a prescription has been sent to a pharmacy. Prescription information may include the user identification information input by the user, the name of a prescribed drug(s), dosing amount, number of refills available, warnings, and instructions on use of the prescribed drug. Diagnosis information and prescription information then may be transmitted over a network, such as Internet 42, and received at analysis apparatus 20. As explained in detail below, apparatus 20 may display diagnosis information and prescription information and may dispense the prescribed drug or print a prescription for the prescribed drug.

Diagnostic system 10 may be used to analyze a variety of biological specimens including, but not limited to, blood, earwax, feces, mucus, saliva, and urine at apparatus 20 to allow a doctor to diagnose a variety of diseases and infections including, but not limited to, bronchitis, diarrhea, diphtheria, ear infections, food poisoning, gonorrhea, leprosy, Lyme disease, meningitis, pink eye, pneumonia, sinus infections, strep throat, syphilis, tetanus, tuberculosis, typhoid fever, ulcers, urinary tract infections, whooping cough, yeast infections, acute nonbacterial disease, and chronic nonbacterial disease. Advantageously, a condition may be diagnosed by a doctor at a location remote from a user at apparatus 20 and the condition may be treated by providing the user with a prescription and/or medication.

Apparatus 20 also may be configured to analyze blood glucose levels and dispense insulin or glucose-lowering drugs, or to dispense medications appropriate for treating patients suffering from a cardiac condition.

Analysis apparatus 20 may include user interface 21, payment unit 22, identification unit 23, and printer 24 enclosed in housing 25 having analyzer opening 26 and medication opening 28 formed therein. Optionally, apparatus 20 may include video camera 35 that enables the user and a doctor at remote doctor workstation 40 to carry on a face-to-face consultation.

User interface 21 is configured to receive user input and to display various menus and data input screens to a user relating to the operation of analysis apparatus 20. User interface 20 may include a visual display screen, a standard alphanumeric key board, a mouse or pointing device, a touch screen, a speaker, a microphone, a webcam and/or a voice recognition device. A user may input user identification information, e.g., name, address, height, weight, insurance information, into user interface 21. A user may also input information relating to symptoms, allergies, doctor information, payment information, medical history, and medication history. A user may input the information by, for example, answering a set of displayed questions and/or filling out a pre-stored electronic medical form. In one embodiment, a user may enter user identification information and additional input using user interface 21 for processing by payment processing center 41, such as billing information and insurance information. A user also could set up an account with the payment processing center via the Internet from a home computer by visiting an online website. Such a website may permit a user to log-in and set up a personalized account that could save the user's identification information, medical history, etc. As will be apparent to one of ordinary skill in the art, although a user is described as providing input to user interface 21 or to a website, the invention is not limited thereto and such information may be provided by a caretaker, doctor, medical personal, colleague, relative, friend, and the like.

Payment unit 22 is configured to receive payment from a user for use of apparatus 20 including payment for any medication dispensed to the user. Payment unit 22 may include a magnetic stripe reader for reading credit and debit cards, and a section for receiving cash and checks as is known in the art of vending and ATM machines. Payment unit 22 is configured to transfer the information to payment processing center 41 to authorize the transaction.

Identification unit 23 is configured to identify the user. Identification unit 23 may include a magnetic stripe reader or bar code reader for reading an identification card such as a driver's license, a medical insurance card, a medical history card, a credit card, and a debit card. Identification unit 23 further may include more complex devices such as, but is not limited to, a finger print scanner, a retinal scanner, a facial recognition device, and/or a DNA scanner.

Printer 24 is configured to print text and graphics. Specifically, printer 24 may be used to print medication prescriptions, diagnosis information, analysis information, instructions for medication use, and receipts.

Housing 25 is configured to house the components of apparatus 20. Housing 25 may be constructed in any number of shapes and modified to be aesthetically pleasing. Housing 25 may include analyzer opening 26 and medication opening 28 formed therein. Analyzer opening 26 is configured to receive a biological specimen and includes door 27 for covering the opening. In one embodiment, analyzer opening 26 is configured to receive a tray assembly described below with reference to FIG. 3. Medication opening 28 is configured to allow a user to retrieve dispensed medication.

Figure 2:
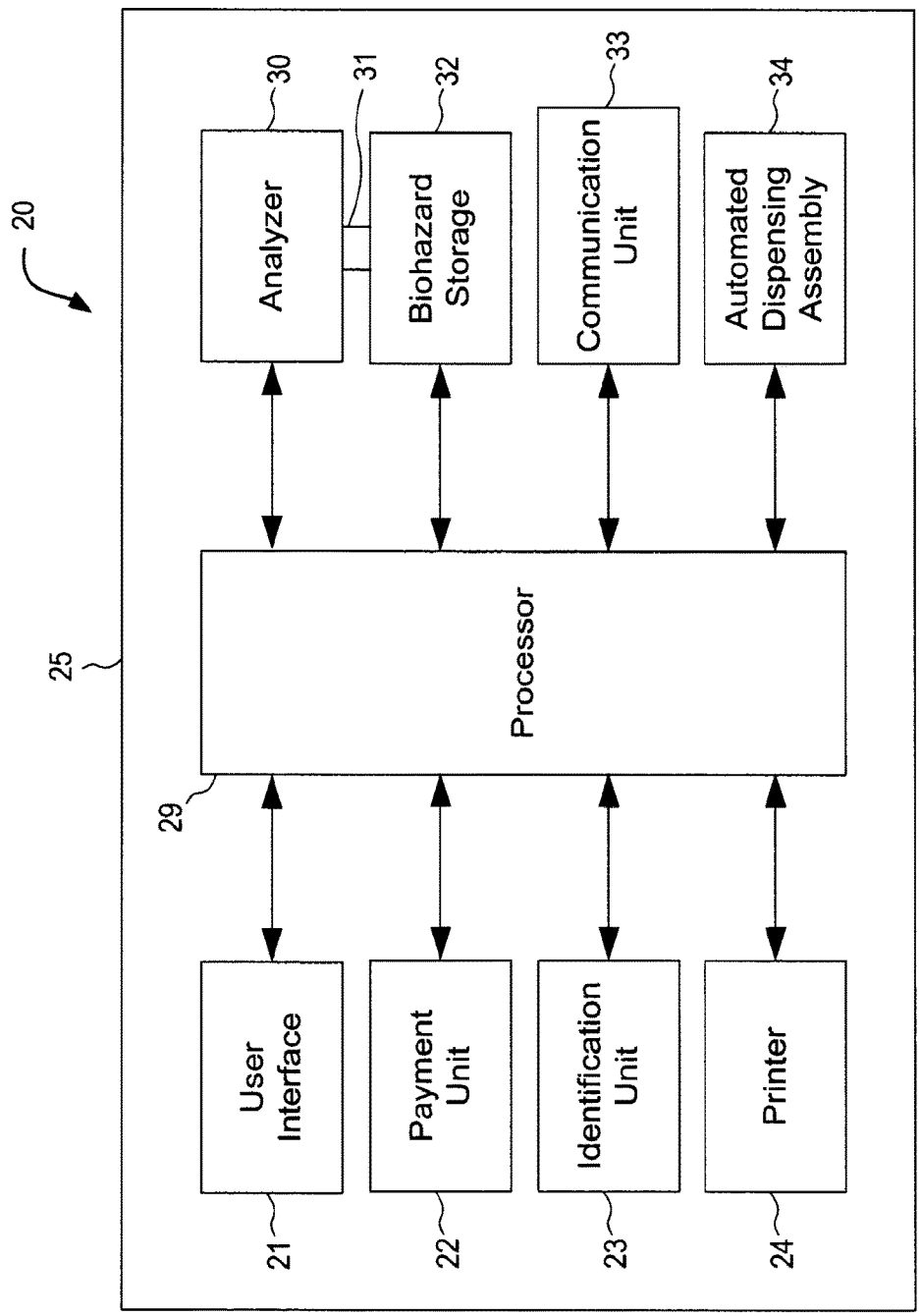
FIG. 2 is a schematic diagram of an analysis apparatus for use in the diagnostic system.

Referring now to FIG. 2, further detail on analysis apparatus 20 is provided. Apparatus 20 includes processor 29 that may be electrically coupled to, and configured to control, user interface 21, payment unit 22, identification unit 23, printer 24, analyzer 30, biohazard storage 32, communication unit 33, and automated dispensing assembly 34.

Processor 29 may include any one or more microprocessors, controllers, digital signal processors (DSPs), application specific integrated circuits (ASICs), field-programmable gate arrays (FPGAs), or equivalent discrete or integrated digital or analog logic circuitry, and the functions attributed to processor 29 herein may be embodied as software, firmware, hardware, or any combination thereof. Processor 29 may include a memory for storing data related to use of apparatus 20, such as medication inventory, user input, payment information, diagnosis information, analysis information, instructions for medication use, transaction logs, electronic medical forms, and the like. The memory may store program instructions that, when executed by processor 29, cause the processor 29 and apparatus 20 to provide the functionality ascribed to them herein. The memory of processor 29 also may store software downloaded thereon or implemented as a program product and stored on a tangible storage device such as machine-readable medium, e.g., tape, compact disk (CD), digital versatile disk (DVD), blu-ray disk (BD), and so forth, external nonvolatile memory device, cloud storage, or other tangible storage medium. The software may include computer executable instructions for controlling apparatus 20. Processor 29 may be configured to store and forward analysis information from analyzer 30 over a wired/wireless network or via computer readable storage such as a flash drive or memory card and to receive prescription information over a wired/wireless network or via computer readable storage.

Analyzer 30 is configured to receive a biological specimen from a user and to analyze the biological specimen to generate analysis information. Analyzer 30 is configured to analyze a variety of biological specimens including blood, earwax, feces, mucus, saliva, and urine. The biological specimen may be placed on a carrier, such as a reagent strip, and inserted into analyzer 30 through the analyzer opening Analyzer 30 may analyze the biological specimen in a manner known to one of ordinary skill in the art to determine analysis information including information on leukocytes, glucose, bilirubin, ketone, specific gravity, nitrite, pH, protein, urobilinogen, blood, albumin, creatinine, leukocyte esterase, red blood cells, white blood cells, and/or bacteria in the biological specimen. Analyzer 30 may include a reflectance spectroscope, or "reflectometer," for optically inspecting the biological specimen as described in detail below with respect to FIGS. 3 through 6.

After a biological specimen is analyzed by analyzer 30, the specimen may be transferred through chute 31 to biohazard storage 32. Biohazard storage 32 may be a container compliant with regulations for storing biohazardous material. Biohazard storage 32 may include a sensor for determining when storage 32 has reached, or nearly reached capacity at which point a signal may be sent to processor 29. Processor 29 then may direct apparatus 20 to power off or alert maintenance audibly or over a network.

Communication unit 33 is configured to transmit the user input including user identification information from user interface 21 and/or identification unit 23 and the analysis information from analyzer 30 to remote doctor workstation 40 and payment processing center 41. The doctor may make a diagnosis based on the analysis information and determine a proper prescription for treating the diagnosed condition via remote doctor workstation 40. The doctor then transmits diagnosis information and prescription information over a network to communication unit 33. In one embodiment, communication unit 33 transmits prescription information to a pharmacy over a private, local network because, for example, apparatus 20 is located in a drugstore having a pharmacy.

Communication unit 33 is configured for wired and/or wireless communication over a network such as the Internet or a telephone network. In one embodiment, communication unit 33 is operatively coupled to a telephone disposed on or adjacent to apparatus 20 allowing a user to have a telephone conversation with the doctor. In another embodiment, communication unit 33 is operatively coupled to a webcam associated with user interface 21 allowing a user to have a video-based conversation with the doctor. In yet another embodiment, communication unit 33 is configured to transmit and receive instant messages and text messages that are displayed on user interface 21 to a doctor using a computer or cellular phone.

Automated dispensing assembly 34 is configured to store and dispense medication based on prescription information from the doctor received at communication unit 33. The medication stored at automated dispensing assembly 34 may include, for example, antibiotics, antispasmodics, glucose lowering drugs, heart medications, and the like. Automated dispensing assembly 34 may include a vault for securely storing medication in compliance with government regulations. Automated dispensing assembly 34 is configured to identify medication corresponding to the prescribed medication in the prescription information in its stored location and to dispense the medication using techniques known in the art of medication dispensing and in vending machine technology. Automated dispensing assembly 34 may, for example, drop the identified medication into medication opening 28 shown in FIG. 1 in a manner similar to that of previously-known vending machines.

In operation, with reference to FIGS. 1 and 2, apparatus 20 is positioned in a suitable location, such as a restroom at a 24-hour pharmacy. A user suspecting to have a medical condition may approach apparatus 20 and provide user input, e.g., user identification information, medical history, etc., into user interface 21. If required, a user may provide further identification information at identification unit 23. User interface 21 may display a message requesting a biological specimen and display instructions for submitting the biological specimen. A specimen container having a reagent strip therein may be provided to a user using automated dispensing assembly 34 or the container may be disposed on or adjacent to apparatus 20. The user then provides the biological specimen in the container, including dipping the reagent strip in the biological specimen, if appropriate. The container then is placed in analyzer opening 26 for analysis of the biological specimen at analyzer 30 and disposal in biohazard storage 32. Alternatively, the user may dump the biological specimen into, for example, a toilet and place the container in a suitable trash receptacle. The reagent strip is placed in analyzer opening 26 to initiate analysis of the biological specimen at analyzer 30 and disposal in biohazard storage 32. Analyzer 30 analyzes the biological specimen to generate analysis information. The user input and the analysis information are transmitted over a network such as Internet 42, using communication unit 33, to remote doctor workstation 40 for review. A doctor reviews the user input and the analysis information to make a diagnosis. The doctor transmits the diagnosis and prescription information over the network so that the information is received at communication unit 33 of apparatus 20 and/or at a pharmacy. The diagnosis and prescription information may be displayed on user interface 21 for a user to review and ask the doctor any questions. A user may provide payment information for use of apparatus 20 using user interface 21 or payment unit 22 with information transmitted to payment processing center 41. Processor 29 directs printer 24 to print a medication prescription based on the prescription information and/or directs automated dispensing assembly 34 to dispense a medication stored therein based on the prescription information.

Referring now to FIGS. 3 through 6, an exemplary embodiment of analyzer 30 is provided, wherein analyzer 30 comprises a reflectance spectroscope, or "reflectometer," similar to that described in the above-referenced Krauth application for analyzing a biological specimen disposed on a reagent strip. The reflectance spectroscope may use a readhead, such as readhead 80 shown in FIGS. 5 and 6, to analyze a reagent strip that is disposed in a tray, such as tray assembly 50 shown in FIGS. 3 and 4.

Figure 3:
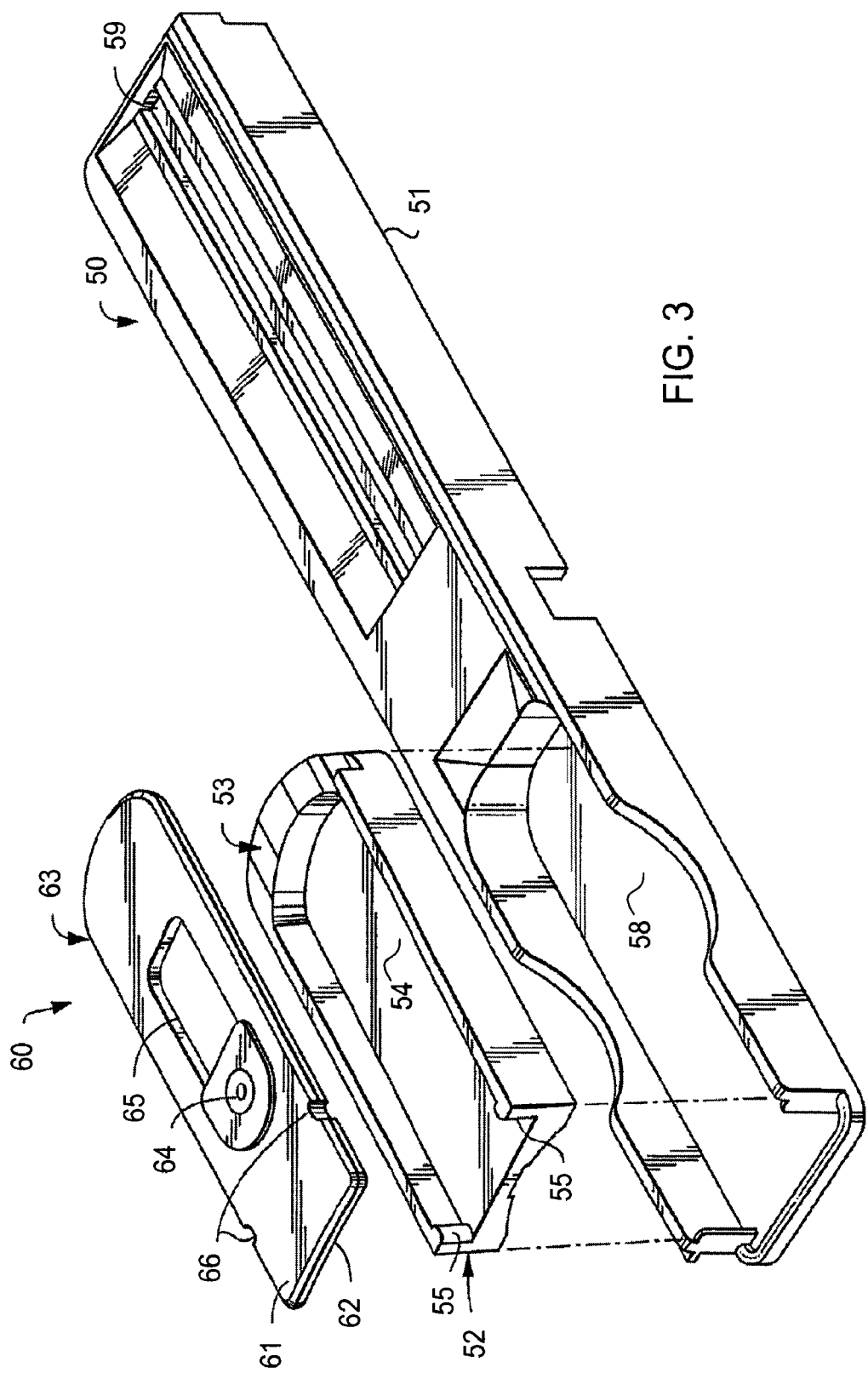
FIGS. 3 and 4 show perspective, exploded views of an exemplary tray assembly for insertion in the analysis apparatus of FIG. 2, wherein an insert is positioned to hold a reagent cassette in FIG. 3 and positioned to hold a reagent strip in FIG. 4.
Figure 4:
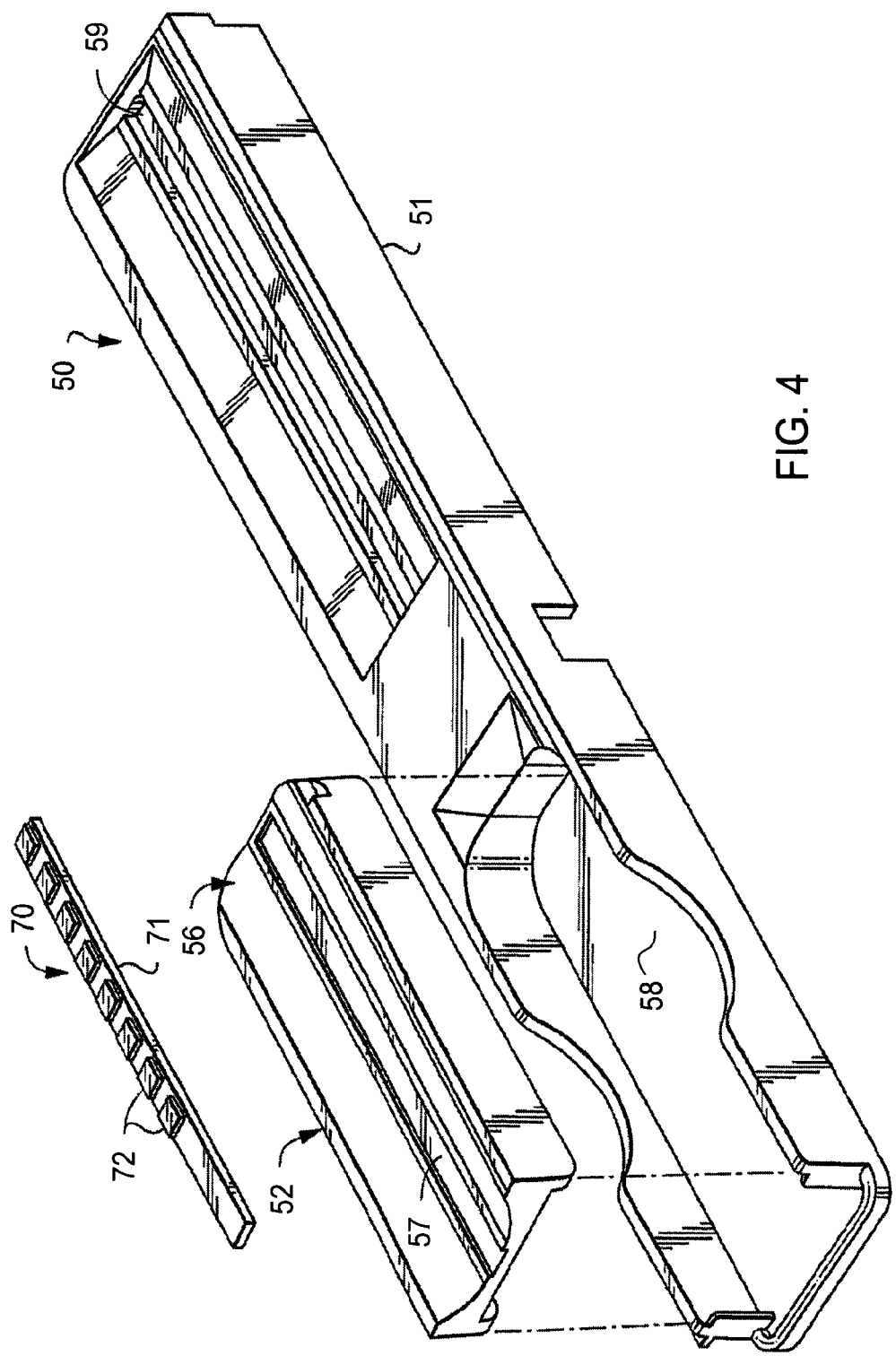

FIGS. 3 and 4 show an exemplary tray assembly 50 for supporting reagent cassette 60 or reagent strip 70. Tray assembly 50 is configured to be inserted in analyzer opening 26 for analysis by analyzer 30. As would be understood by one of ordinary skill in the art, many different designs and configurations of trays may be utilized for insertion in analyzer opening 26. Tray assembly 50 may include support tray 51 and insert 52 that fits into support tray 51 with one of first surface 53 (FIG. 3) and second surface 56 (FIG. 4) facing upwardly so that one of reagent cassette 60 (FIG. 3) or reagent strip 70 (FIG. 4) may be held by insert 52 in support tray 51. First surface 53 of tray assembly 50 is configured to hold reagent cassette 60 as shown in FIG. 3 and second surface 56 is configured to hold reagent strip 70 as shown in FIG. 4.

Referring to FIG. 3, reagent cassette 60 may be a disposable, single-use cassette for doing a conventional lateral flow test. Reagent cassette 60 may have housing 63 including top piece 61, which defines window 65, secured to bottom piece 62. Reagent cassette 60 may have an opening or well 64 in top piece 62 into which a biological specimen, such as urine, is placed. Housing 63 of reagent cassette 60 contains a reagent strip (not shown) which may react with the biological specimen placed in well 64. Depending on the results of the test, the reagent strip may change color, e.g., a colored stripe may appear, which may be determinable from viewing the reagent strip through window 65 of reagent cassette 60.

Referring to FIG. 4, reagent strip 70 may have a thin, non-reactive substrate 71 on which a number of reagent pads 72 are fixed. Each reagent pad 72 may be composed of a relatively absorbent material impregnated with a respective reagent, each reagent and reagent pad 72 being associated with a particular test to be performed. When urinalysis tests are performed, for example, they may include a test for leukocytes in the urine, a test of the pH of the urine, a test for blood in the urine, etc. When each reagent pad 72 comes into contact with a urine sample, the pad changes color over a time period, depending on the reagent used and the characteristics of the urine sample. Reagent strip 70 may be, for example, a MULTISTIX® reagent strip commercially available from Bayer Corporation, Diagnostics Division, of Tarrytown, N.Y., and reagent strip 70 may include, but is not limited to, reagent pads 72 for: leukocytes, glucose, bilirubin, ketone, specific gravity, nitrite, pH, protein, urobilinogen, blood, albumin, and creatinine.

During use, insert 52 of tray assembly 50 is removable from support tray 51 and may be turned over and re-inserted into support tray 51 depending upon which of reagent cassette 60 and reagent strip 70 is to be used. Referring to FIG. 3, surface 53 of insert 52 has recess 54 shaped to receive reagent cassette 60. An end wall of recess 54 may be curved to match a curved end wall of reagent cassette 60, to ensure that a user correctly orients reagent cassette 60 within insert 52. Insert 52 also may include orientation features such as bosses 55 that are received in, respectively, indents 66 in reagent cassette 60 to prevent reagent cassette 60 from sliding out of insert 52. Alternatively, the bosses may be provided on reagent cassette 60 and the indents in insert 52. Bosses 55 of recess 54 may be provided in slightly different sizes or shapes, and indents 66 of reagent cassette 60 may also be provided in slightly different sizes or shapes, which match bosses 55, to prevent reagent cassette 60 from being inserted into insert 52 upside down.

Referring now to FIG. 4, second surface 56 of insert 52 includes elongated channel 57 sized to accommodate reagent strip 70. As shown in FIGS. 3 and 4, support tray 51 includes compartment 58 for receiving insert 52, and optional elongated channel 59 for receiving a white calibration strip (not shown).

Figure 5:
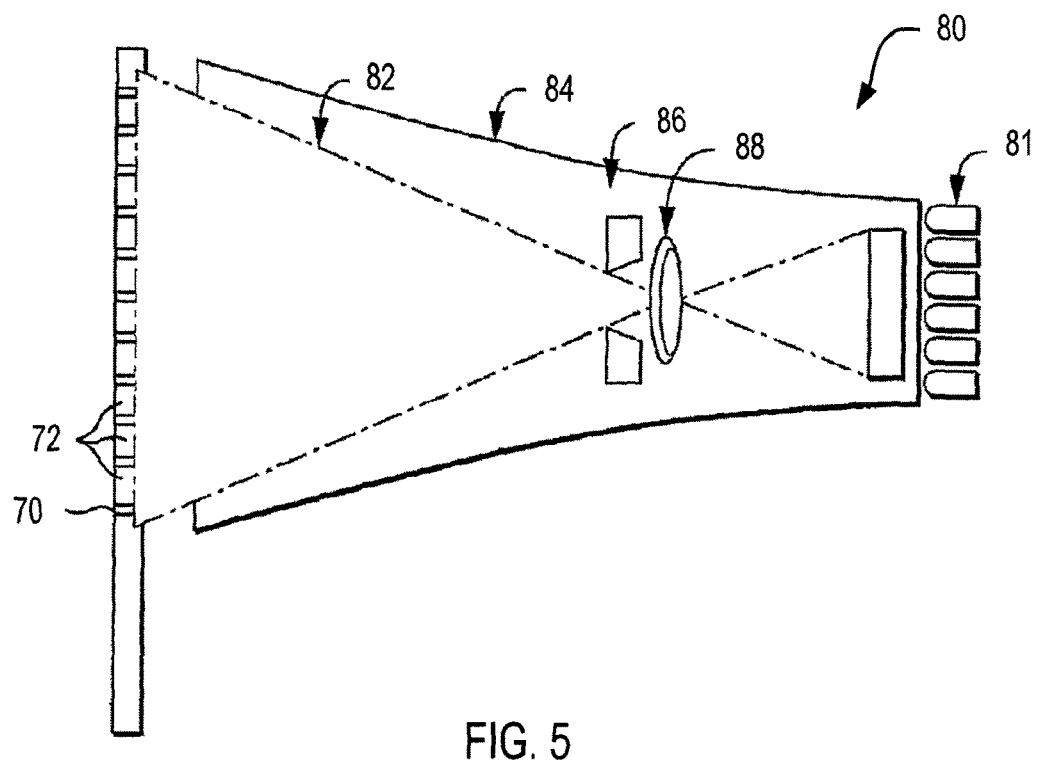
FIG. 5 shows a top plan view of a diagram illustrating an exemplary readhead of an analyzer of the analysis apparatus of FIG. 2.
Figure 6:
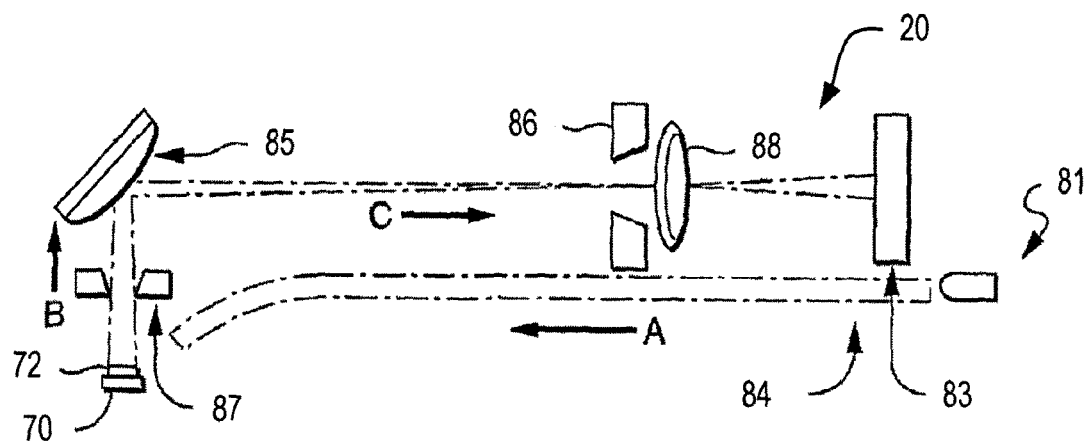
FIG. 6 shows a side elevation view of a diagram illustrating the readhead of FIG. 5.

FIGS. 5 and 6 show an exemplary readhead 80 of analyzer 30 for analyzing a biological specimen disposed on a reagent strip. Readhead 80 may include light-emitting diodes (LEDs) 81 for emitting light 82, detector array 83, waveguide 84, mirror 85, apertures 86 and 87, and aspheric lens 88.

LEDs 81 may be configured to irradiate a specimen with light 82 at a number of different wavelengths. For example, the signals transmitted by the LEDs may be blue light at a wavelength of about 470 nanometers (nm), green light at a wavelength of about 525 nm, green light at a wavelength of about 565 nm, red light at a wavelength of about 625 nm, red light at a wavelength of about 660 nm, and an infrared (IR) signal at a wavelength of about 845 nm. As would be understood by one of ordinary skill in the art, these wavelengths are approximate and that LED manufacturers typically provide LEDs that operate within a specified range of light output. In operation, one of LEDs 81 functions at a time, and the illumination provided by a single LED 81 is sufficient to uniformly illuminate reagent strip 70 to an extent that allows detector array 83 to detect enough light from reagent strip 70 for analysis. Detector array 83 may include any number of suitable photodetectors, e.g., photodiodes operative at one or more wavelengths of the source LEDs.

Test signals from LEDs 81 are transmitted through waveguide 84 in the direction of arrow A, as shown in FIG. 6. The test signals from waveguide 84 impinge on one of a reagent cassette or a reagent strip positioned in readhead 80 on the tray assembly (not shown in FIGS. 5 and 6). In FIGS. 5 and 6, reagent strip 70 is shown positioned in the readhead 80. Light reflected from the test strip in the direction of arrow B, as shown in FIG. 6, passes through aperture 87, after which it impinges on convex mirror 85, which redirects and focuses the reflected signals in the direction of arrow C, as shown in FIG. 6. In this arrangement, due to the orientation of mirror 85, the optical path of the reflected signals takes an approximate 90° turn after leaving reagent strip 70. The reflected signals propagating in the direction of arrow C pass through aperture 86 and converge at aspheric diverging lens 88. Aspheric lens 88 spreads the reflected signals, which then impinge on detector array 83. As will be appreciated by those skilled in the art, the shapes and arrangement of mirrors and lenses need not specifically conform to or be limited to those shown in the illustrative embodiment of FIGS. 5 and 6.

Detector array 83 receives the optical signals reflected from the reagent cassette or strip of test pads 72. The reflected image of the reagent cassette or strip of test pads 72 as detected at detector array 83 represents the reflectance values of the reagent cassette or strip. The individual detectors of detector array 83 may convert the received optical signals into electrical signals for image processing at, for example, processor 29 shown in FIG. 2. In one embodiment, detector array 83 is a charge coupled device (CCD) including a linear arrangement of 2048 detectors configured to receive the reflected signals. Signals produced by detector array 83 may be used on a detector-by-detector basis to form a usable representation, e.g., an array of discrete, digitized values, of test pads 72. Picture element (pixel) data may be grouped and associated with individual pads 72 on reagent strip 70. As a result, reagent strip may be imaged and wavelength-specific reflectance values for each pad may be determined, for example, according to the following description.

The received reflected signals, as an image of the test strip at various wavelengths, represent an optical spectral signature of the test pad. A spectral signature is a plot of reflectance, e.g., as a percentage of the incident light, versus wavelength for a given material. The reflected signals received by the detectors may be translated into data, e.g., in digital form, representing the reflectance values and optical signature. Each reflectance value is a function of the wavelength of the light transmitted from the source and the make-up of the test pad from which the signal was reflected. Accordingly, different specimens and test pads may have different spectral signatures. For reflected signals received at the detector, the presence of a material associated with a particular spectral signature may be determined by comparing the reflected signals with a set of know spectral optical signatures. As a result, various information on a biological specimen may be determined during analysis including information on leukocytes, glucose, bilirubin, ketone, specific gravity, nitrite, pH, protein, urobilinogen, blood, albumin, creatinine, leukocyte esterase, red blood cells, white blood cells, and/or bacteria in the biological specimen.

Figure 7:
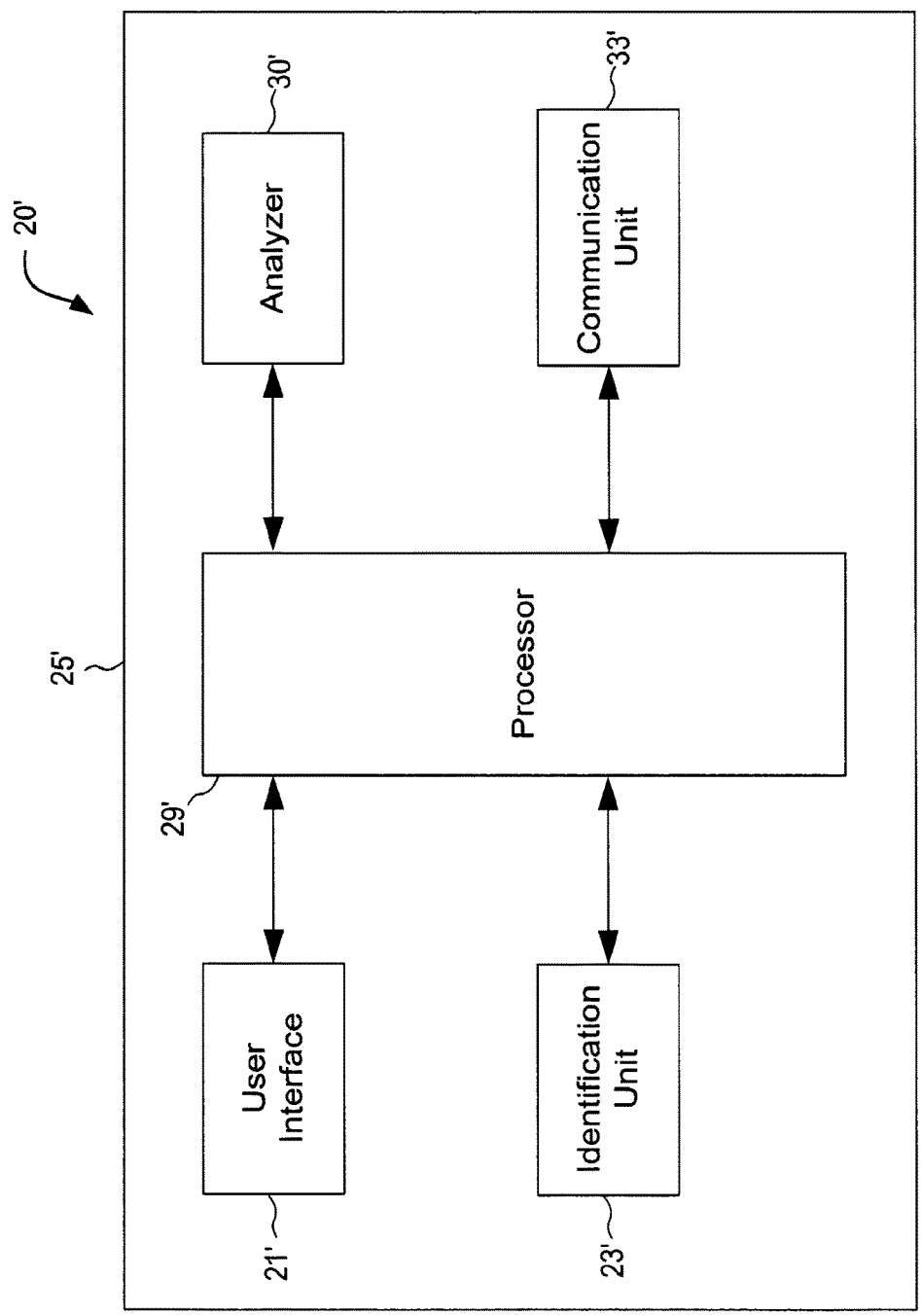
FIG. 7 is a schematic diagram of an alternative analysis apparatus for personal or home use in the diagnostic system.

Referring now to FIG. 7, alternative analysis apparatus 20' for use in a diagnostic system constructed in accordance with the principles of the present invention is described. Analysis apparatus 20' may be substituted for analysis apparatus 20 of diagnostic system 10 of FIG. 1. Analysis apparatus 20' includes components similar to the components in analysis apparatus 20 of FIG. 1, wherein like components are identified by like-primed reference numbers. Thus, for example, user interface 21' in FIG. 7 corresponds to user interface 21 of FIG. 1, processor 29'in FIG. 7 corresponds to processor 29 of FIG. 1, etc. As will be observed by comparing FIGS. 1 and 7, analysis apparatus 20' need not necessarily include a payment unit, a printer, biohazard storage, or an automated dispensing assembly. Additionally, housing 25' may be sized, shaped, and configured for personal and/or home use such as, for example, a handheld configuration.

Apparatus 20' may be obtained from a suitable retailer or medical entity, such as a pharmacy, grocery store, doctor, hospital, clinic, etc. A user suspecting he or she has a medical condition may use apparatus 20' in a suitable location, such as their home or other private place. The user may provide user input, e.g., user identification information, medical history, etc., via user interface 21' or alternatively, may provide user input via a website associated with the system using a personal computer located elsewhere. If required, a user may provide further identification information at identification unit 23'. User interface 21' may display a message requesting a biological specimen and display instructions for submitting the biological specimen or instructions for use may be provided with purchase of apparatus 20'. A specimen container having a reagent strip therein may be provided to a user with apparatus 20' or may be sold separately. A user then may provide the biological specimen in the container and may dip the reagent strip in the biological specimen. The reagent strip may be placed in analyzer 30' for analysis of the biological specimen and the user may dump the biological specimen into, for example, a toilet and place the container in a suitable trash receptacle. Analyzer 30' analyzes the biological specimen to generate analysis information. The user input and the analysis information are transmitted over a network such as the Internet to a doctor and/or a doctor network for review using communication unit 33'. The user input may alternatively, or additionally, be transmitted to a personal computer that has accessed the website over a wired/wireless network using communication unit 33' or transmitted to the personal computer using computer readable storage such a flash drive or memory card. The appropriate doctor reviews the user input and the analysis information to make a diagnosis. The doctor then transmits, using a suitable computer, diagnosis and prescription information over the network and such information is received at communication unit 33' of apparatus 20', at a personal computer, and/or at a pharmacy. Communication unit 33' may transmit the diagnosis and/or prescription information to a personal computer for printing a medication prescription based on the prescription information. A user then may travel to pharmacy to pick up the medication or have the pharmacy ship the medication.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. An apparatus for dispensing a medication to a user for use in treating a urinary tract infection (UTI) or sexually transmitted disease (STD), the apparatus configured to exchange information via a network, the apparatus comprising:

a housing comprising first and second openings;
a user interface coupled to the housing and configured to receive user identification information input by the user;
an analyzer disposed within the housing and configured to receive a urine specimen from the user via the first opening and configured to optically inspect the urine specimen to generate analysis information indicating whether the user has a UTI or STD;
a payment unit coupled to the housing and configured to receive payment information from the user for use of the apparatus;
a communication unit coupled to the housing;
a processor coupled to the housing and configured to:
  store the analysis information;
  forward the analysis information and the user identification information to a doctor workstation via the communication unit and the network;
  receive prescription information from the doctor workstation via the communication unit and the network after forwarding the analysis information and the user identification information, wherein, based upon the analysis information indicating that the user has a UTI or STD, the prescription information includes a dosing amount of the medication;
a display coupled to the housing and configured to display the prescription information to the user; and
an automated dispensing assembly disposed within the housing, the automated dispensing assembly storing the medication, the automated dispensing assembly dispensing to the user, via the second opening, the stored medication corresponding to the prescription information.

2. The apparatus of claim 1, further comprising a printer configured to print a medication prescription based on the prescription information.

3. The apparatus of claim 1, wherein the user interface comprises an identification unit configured to identify the user, the identification unit having a magnetic stripe reader.

4. The apparatus of claim 1, wherein the analyzer comprises a reflectance spectroscope.

5. The apparatus of claim 1, wherein the analyzer is configured to receive the urine specimen on a reagent strip from the user and to optically inspect the urine specimen on the reagent strip.

6. The apparatus of claim 1, wherein the analysis information comprises information on any one of leukocytes, glucose, bilirubin, ketone, specific gravity, nitrite, pH, protein, urobilinogen, blood, albumin, creatinine, leukocyte esterase, red blood cells, white blood cells, bacteria, or any combination thereof in the urine specimen.

7. A system for dispensing a medication to a user for use in treating a urinary tract infection (UTI) or a sexually transmitted disease (STD), the system comprising:
a remote doctor workstation;
a payment processing center; and
an apparatus comprising:
a housing comprising first and second openings;
a user interface coupled to the housing and configured to receive user identification information input by the user;
an analyzer disposed within the housing and configured to receive a urine specimen from the user via the first opening and configured to optically inspect the urine specimen to generate analysis information indicating whether the user has a UTI or STD;
a payment unit coupled to the housing and configured to receive payment information from the user for use of the apparatus;
a communication unit coupled to the housing;
a display coupled to the housing;
a processor configured to:
transmit the user identification information and the analysis information via the communication unit and over a network to the remote doctor workstation,
transmit the user identification information and the payment information to the payment processing center over the network; and
receive prescription information from the doctor workstation via the communication unit after transmitting the user identification information and the analysis information, wherein, based upon the analysis information indicating that the user has a UTI or STD, the prescription information includes a dosing amount of the medication; and
cause the display to display the prescription information to the user; and an automated dispensing assembly disposed within the housing,
the automated dispensing assembly storing the medication,
the automated dispensing assembly dispensing to the user, via the second opening, the stored medication corresponding to the prescription information.

8. A method for dispensing, by an apparatus, a medication to a user for use in treating a urinary tract infection (UTI) or sexually transmitted disease (STD), the method comprising:
receiving, by a user interface coupled to a housing of the apparatus, user identification information entered by the user;
receiving, by a payment unit coupled to the housing, payment information from the user for use of the apparatus;
receiving via a first opening of the housing, by an analyzer disposed within the housing, a urine specimen from the user;
optically inspecting, by the analyzer, the urine specimen to generate analysis information indicating whether the user has a UTI or STD;
transmitting, by a communication unit coupled to the housing, the analysis information over a network to a doctor workstation for diagnosis;
receiving from the doctor workstation, by the communication unit, prescription information based on the diagnosis, wherein based upon the analysis information indicating that the user has a UTI or STD, the prescription information includes a dosing amount of the medication;
displaying, by a display coupled to the housing, the prescription information to the user;
storing the medication by an automated dispensing assembly within the housing; and
dispensing to the user via a second opening of the housing, by the automated dispensing assembly, the stored medication corresponding to the prescription information.

9. The method of claim 8, further comprising printing, by a printer of the apparatus, a medication prescription based on the prescription information.

10. The method of claim 8, wherein transmitting the analysis information over the network comprises:
transmitting, by the communication unit, the analysis information to computer readable storage,
inputting the computer readable storage into a computer, and
transferring the analysis information over the network from the computer to the doctor workstation.

11. The method of claim 8, further comprising:
transmitting, by the doctor workstation, the prescription information to a computer over the network, and
transferring the prescription information to computer readable storage.

12. The method of claim 8, wherein the analyzer comprises a reflectance spectroscope.

13. The method of claim 8, wherein the analyzer optically inspects the urine specimen on a reagent strip.

14. The method of claim 8, wherein the analysis information comprises information on any one of leukocytes, glucose, bilirubin, ketone, specific gravity, nitrite, pH, protein, urobilinogen, blood, albumin, creatinine, leukocyte esterase, red blood cells, white blood cells, bacteria, or any combination thereof in the urine specimen.

15. The method of claim 8, wherein the STD includes any one of gonorrhea, leprosy, syphilis, a yeast infection, acute nonbacterial disease, chronic nonbacterial disease, or any combination thereof.

16. The method of claim 8, wherein the medication is an antibiotic or an antispasmodic.

17. The apparatus of claim 1, wherein the medication is an antibiotic or an antispasmodic.

18. The system of claim 7, wherein the medication is an antibiotic or an antispasmodic.

\* \* \* \* \*